United States Patent [19]

McDonough et al.

[11] Patent Number: 5,380,524
[45] Date of Patent: Jan. 10, 1995

[54] SEX ATTRACTANT FOR THE APPLE ERMINE MOTH

[75] Inventors: Leslie M. McDonough; Harry G. Davis, both of Yakima, Wash.

[73] Assignee: The United States of America as represented by the Secretary of Agriculture, Washington, D.C.

[21] Appl. No.: 3,948

[22] Filed: Jan. 4, 1993

Related U.S. Application Data

[63] Continuation of Ser. No. 552,387, Jul. 13, 1990, abandoned.

[51] Int. Cl.6 .......................................... H01N 25/00
[52] U.S. Cl. ....................................................... 424/84
[58] Field of Search ........................................ 424/84

[56] References Cited

PUBLICATIONS

L. M. McDonough, H. G. Davis, and S. Voerman, "Blackheaded Fireworm: Laboratory and Field Studies of its Sex Pheromone," *Journal of Chemical Ecology* 13: 1235–1242 (1987).

van der Pers and den Otter, "Single Cell Responses from Olfactory Receptors of Small Ermine Moths to Sex-Attractants,"*Journal of Insect Physiology* 24:337–343 (1978).

Lofstedt et al., "Evolution of the Ermine Moth Pheromone Tetradecyl Acetate,"*Nature* 323:621–623 (1986).

Hendrikse, "Intra–and Interspecific Sex–Pheromone Communication in the Genus *Yponomeuta*," *Physiological Entomology* 11: 159–169 (1986).

Hendrikse et al., "Sex Pheromones, Attractants and Inhibitors in Small Ermine Moths: A Comparison of Bioassays," *Med. Fac. Landbouww, Rijksuniv. Gent.* 47: 493–502 (1982).

Arn et al., "Sex Attractant Inhibitors of the Codling Moth *Laspeyresia pomonella* L.," *Experientia* 30: 1142–1143 (1974).

Lofstedt and van der Pers, "Sex Pheromones and Reproductive Isolation in Four European Small Ermine Moths," *Journal of Chemical Ecology*, 11: 649–666 (1980).

Lofstedt and Herrebout, "Sex Pheromones of Three Small Ermine Moths Found on the European Spindle Tree," *Entomol. Exp. Appl.* 46: 29124 38 (1988).

Yamamoto et al 111, CA:129027d 1987.

Ogawa et al 111 CA: 73091a 1988.

*Primary Examiner*—Raymond J. Henley, III
*Assistant Examiner*—Russell Travers
*Attorney, Agent, or Firm*—M. Howard Silverstein; John D. Fado; Margaret A. Connor

[57] ABSTRACT

A composition of two compounds, (Z)-11-tetradecen-1-ol and (Z)-9-dodecen-1-ol acetate, in a ratio of 100:0.3 to 100:2.5 is a highly effective attractant for the male apple ermine moth. The composition demonstrates biological activity toward apple ermine moth males comparable to or greater than that of the apple ermine moth females. By attracting adult males to field traps, the composition provides a means for detecting, monitoring, and controlling this agricultural pest.

6 Claims, 6 Drawing Sheets

SEX ATTRACTANT FOR THE APPLE ERMINE MOTH

This application is a continuation of application Ser. No. 07/552,387, filed Jul. 13, 1990 now abandoned.

BACKGROUND OF THE INVENTION

1. Field of the Invention

The invention relates to a novel composition and use thereof for insect control. More particularly, the invention relates to a composition of (Z)-11-tetradecen-1-ol and (Z)-9-dodecen-1-ol acetate and use of the composition as an attractant, disruptant, and monitoring agent for the apple ermine moth.

2. Description of the Art

The apple ermine moth (*Yponomeuta malinellus* Zeller) is a member of a European group of small ermine moths (Yponomeuta) which have been studied in recent years in order to clarify taxonomic and evolutionary relationships among species within this genus. This group consists of nine species, of which five are classified as members of the "Padellus complex" (Wiebes, Neth. J. Zool. 26: 440 (1975)). The padellus complex consists of *Y. padellus, Y. cagnagellus, Y. mahalebellus, Y. malinellus* (apple ermine moth), and *Y. rorellus*. The other four species are *Y. evonymellus, Y. irrorellus, Y. plumbellus*, and *Y. vigintipunctatus*. Species of the padellus complex are difficult to distinguish morphologically, and other features such as feeding preference and sex pheromones may be used for positive identification (van der Pers and den Otter, *Journal of Insect Physiology* 24: 337-343 (1978)). In flight tunnel and field tests, attractants have been established for seven of the nine species of small ermine moths. The two species for which attractants have not been established are the apple ermine moth and *Y. mahalebellus*. Each of the species of small ermine moth studied showed a species-specific sex pheromone. Lofstedt et al. (*Nature* 323: 621-623 (1986)) reported that identified European small ermine moth sex pheromones were multi-component (2-8 compounds). Each pheromone varied as to number, proportion, and type of compounds present. Compounds identified as components of the sex pheromone gland amongst seven of the species are (Z)- and (E)-11-tetradecen-1-ol acetate, (Z)- and (E)-11-tetradecen-1-ol, tetradecyl acetate, (Z)-11-hexadecen-1-ol acetate, hexadecyl acetate, tetradecan-1-ol.

Previously several attempts to discover the sex pheromone of the apple ermine moth have been carried out. From flight tunnel tests, Hendrikse, *Physiological Entomology* 11: 159-169 (1986), found that apple ermine moth males flew upwind to *Y. evonymellus* females, but terminated response when about 20 cm from them. In measurements of electrophysiological responses to model compounds of single sensilla trichodea on the antennae of male apple ermine moths, van der Pers and den Otter, supra, reported the strongest response was obtained from (Z)-11-tetradecen-1-ol, and moderate responses were obtained from (Z)-11-tetradecen-1-ol acetate, (E)-11-tetradecen-1-ol acetate, and (Z)-9-tetradecen-1-ol acetate. The investigators reported that of the five species of Yponomeuta studied [*Y. cagnagellus, Y. padellus, Y. rorellus*, apple ermine moth (all belonging to the padellus-complex) and *Y. vigintipunctatus*], the remarkably different response spectrum of the apple ermine moth suggested that of the members of the padellus-complex tested, this species diverged most in the speciation process. In an electroantennographic (EAG) profile of all the normal, monoene, 14 carbon acetates, Hendrikse et al., *Med. Fac. Landbouww. Rijksuniv. Gent.* 47: 493-502 (1982), reported that (Z)-11-tetradecen-1-ol acetate gave the strongest response. Although a response profile for the corresponding 14 carbon alcohols or other series was not reported, they reported that (Z)-11-tetradecen-1-ol produced a stronger response than (Z)-11-tetradecen-1-ol acetate. In single cell analysis which measures the response of only one receptor cell of the antennae, they found the strongest response from (Z)-11-tetradecen-1-ol and obtained moderate responses from (Z,E)-9,12-tetradecadien-1-ol acetate, (Z)-11-tetradecen-1-ol acetate, (Z)-11-tetradecenal, (Z)-11-tridecen-1-ol acetate, (Z)-9-tridecen-1-ol acetate, and (Z)-9-dodecen-1-ol acetate. In field studies of chemicals that inhibit codling moth (*Laspeyresia pomonella* L.) attraction, Arn et al. (*Experientia* 30: 1142-1143 (1974)) found that some apple ermine moths were also caught in traps baited with (Z)-11-tetradecen-1-ol acetate. Stockel (*Agronomie* 1:355-358 (1981)) reported that Yponomeuta moths were captured in traps baited with a mixture of (Z)- and (E)-11-tetradecen-1-ol acetate (97:3 Z:E). He believed the captured species to be either the apple ermine moth or *Y. padellus*.

Ermine moths occur in beth Europe and Asia. Interest in the apple ermine moth has increased because of its accidental introduction into British Columbia, Canada in the 1980s and its subsequent spread into Washington State, USA. An effective attractant is needed to detect and monitor populations of apple ermine moths to prevent its spread into commercial apple orchards in Washington State and other apple growing areas in the United States where the pest does not yet occur.

SUMMARY OF THE INVENTION

We have discovered that a composition of two compounds, (Z)-11-tetradecen-1-ol and (Z)-9-dedecen-1-ol acetate, in a particular ratio range, is a highly effective attractant for the male apple ermine moth. The composition demonstrates biological activity toward apple ermine moth males comparable to or greater than that of the apple ermine moth females. The composition of the invention is the first known chemical attractant for this species of small ermine moth, and provides, for the first time, a means for detecting, monitoring, and controlling this species.

The attractant composition of the invention provides a highly effective lure for use to detect and monitor the apple ermine moth so as to prevent spread to other states in the U.S. or to other areas of the world that may be threatened by this pest. Another important use of the invention is for monitoring nursery stock to prevent shipment of stock infested with the apple ermine moth.

The composition is highly effective in attracting male apple ermine moths to traps baited with the composition. An important feature is that it attracts males of the species, and thus is useful for male annihilation. When used in combination with a control agent for the apple ermine moth, such as a pesticide or biological control agent, the composition can be used to attract and incapacitate male moths so that they are not able to fertilize the females. Another use of the composition of the invention as a control agent is for disruption of mating by confusion of apple ermine moths.

In sum, the novel sex attractant composition provides a sensitive tool for the detection of the apple ermine moth and provides a means for population control and population density estimation of this pest. Its usefulness in eliciting a behavioral response when applied to a locus of apple ermine moth males suggests the following economic applications: (1) the detection of infestation outbreaks; (2) the monitoring of existing adult populations in order to predict future infestation levels for scheduling treatment the following year with larval insecticides or for treatment of moths in the current year with conventional pesticides or other control agents; (3) the monitoring of nursery stock, and (4) the control of reproduction in adult populations either by direct disruption of mating through confusing or inhibitory properties, or by attracting a demographically significant portion of the male population for subsequent destruction or sterilization.

In accordance with this discovery, it is an object of the invention to identify for the first time a unique sex attractant composition for the apple ermine moth.

Another object of the invention is the provision of the composition as a detection, monitoring, or control agent for the apple ermine moth.

A further object of the invention is the provision of an apple ermine moth sex attractant for use with insecticides, biological control agents, or other toxicants to attract and combat the pest.

Other objects and advantages of the invention will become readily apparent from the ensuing description.

DETAILED DESCRIPTION OF THE INVENTION

The attractant composition of the invention requires the presence of two compounds, (Z)-11-tetradecen-1-ol (hereinafter I) and (Z)-9-dodecen-1-ol acetate (hereinafter II), in the mixture. The broad range of weight ratios of the compounds in the composition that is an effective attractant for apple ermine moth males is about 100:0.3 to 100:2.5 (I:II). This corresponds to a ratio range of about 99:1 to 91:9 (I:II) in the evaporating vapor when the composition is used in conjunction with a rubber septum as the controlled release substrate. The preferred weight ratio range of the attractant composition is 100:0.5 to 100:1.5 (I:II). This corresponds to a ratio range of about 98:2 to 95:5 (I:II) in the evaporating vapor when the composition is used in conjunction with a rubber septum.

Figure 1:
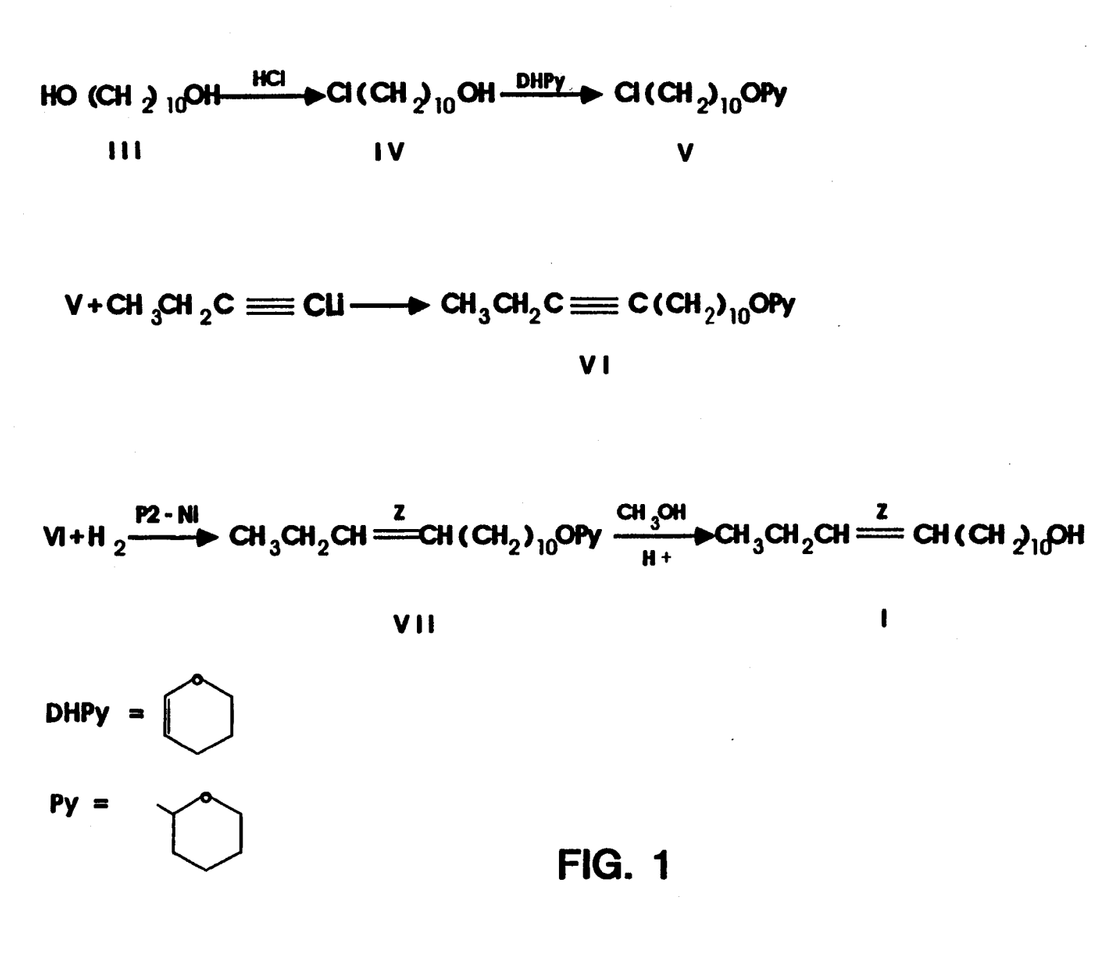
FIG. 1 shows the synthesis of (Z)-11-tetradecen-1-ol (I).
Figure 2:
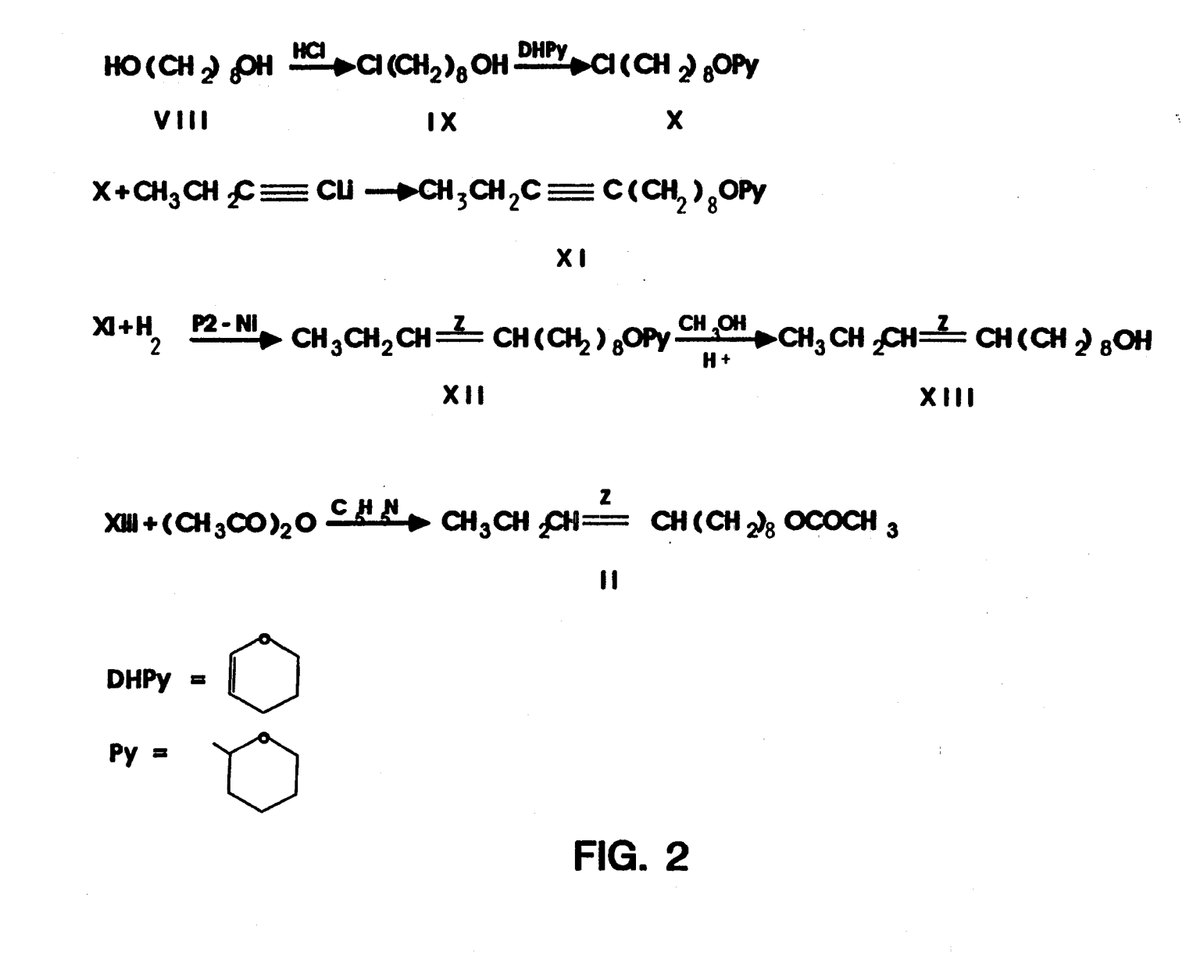
FIG. 2 shows the synthesis of (Z)-9-dodecen-1-ol acetate (II).
Figure 3A:
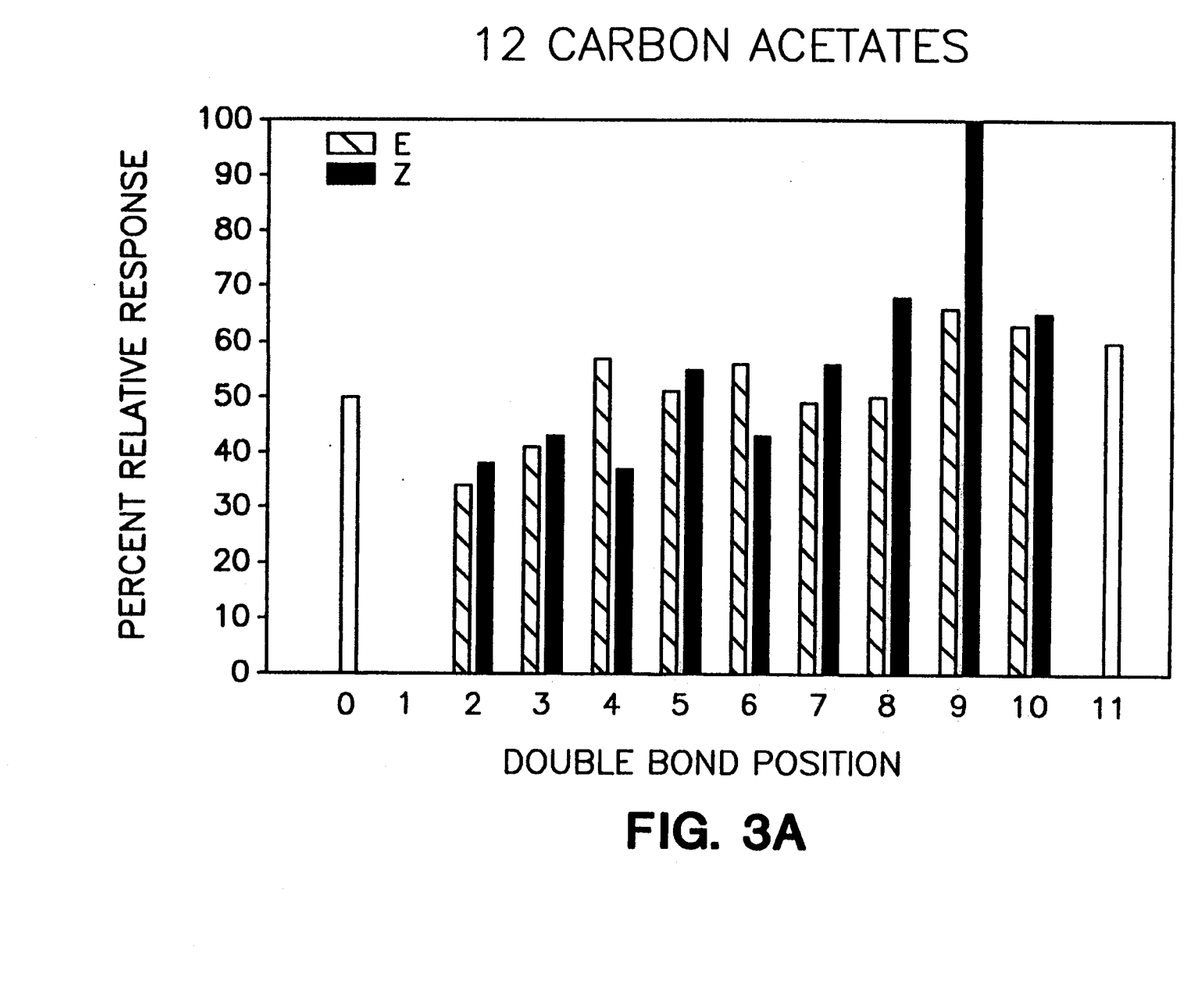
FIGS. 3A–D shows electroantennogram responses of male apple ermine moth to model compounds. Numbers indicate double bond position; zero indicates saturated. Z-isomers are listed after E-isomers.
Figure 3B:
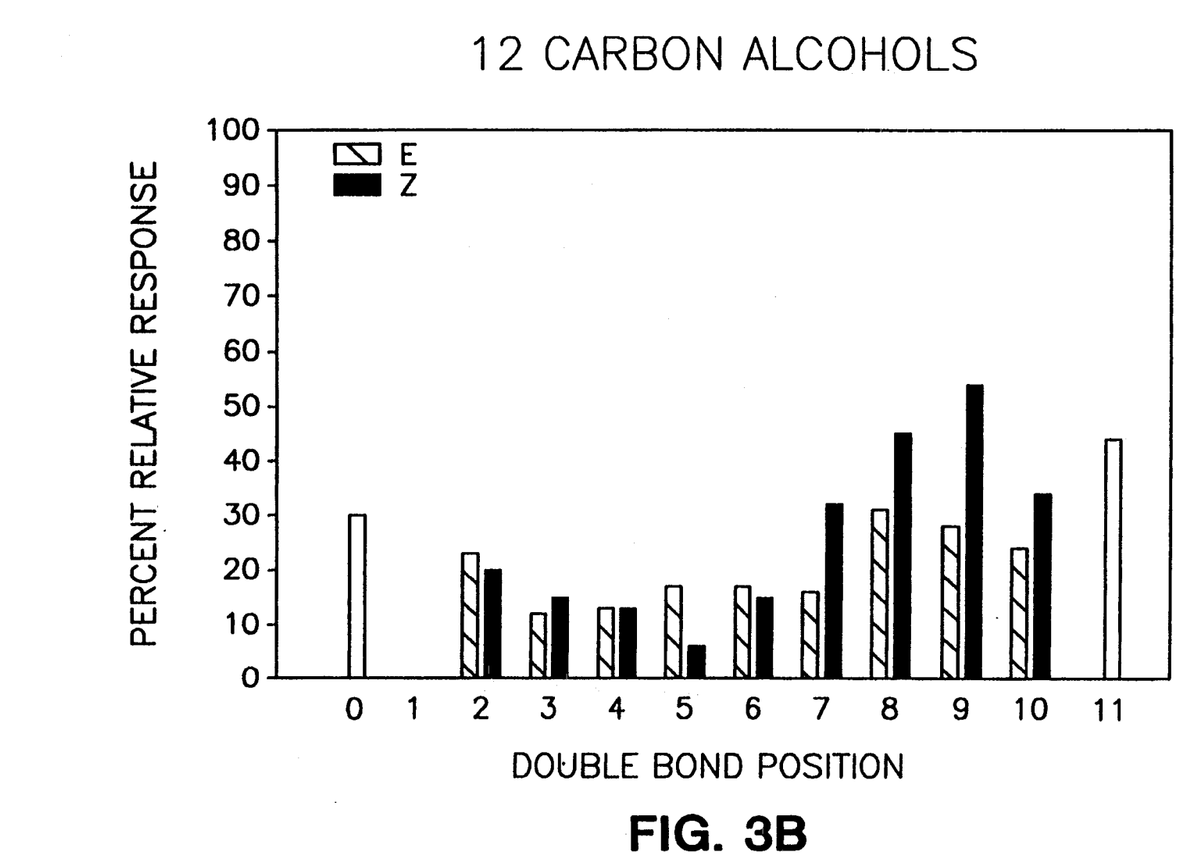
Figure 3C:
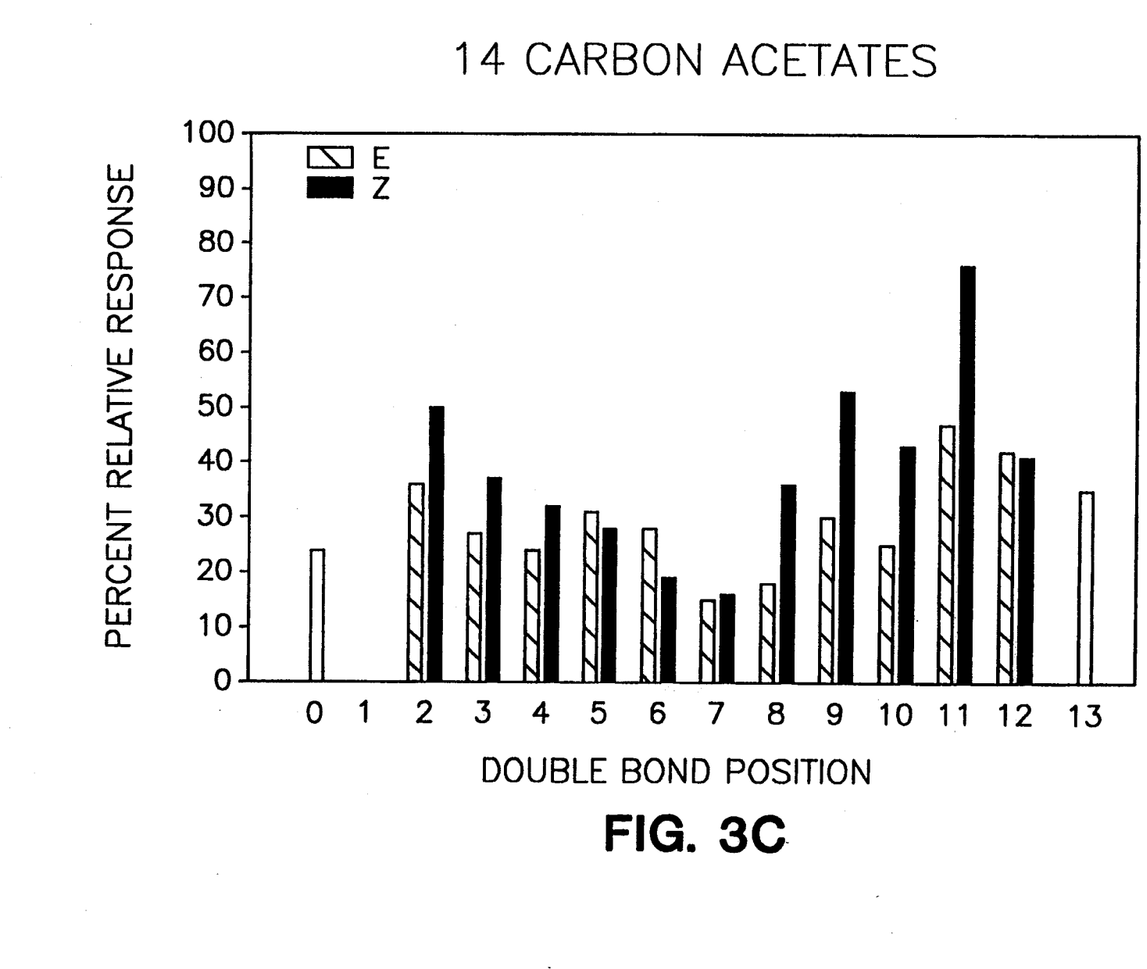
Figure 3D:
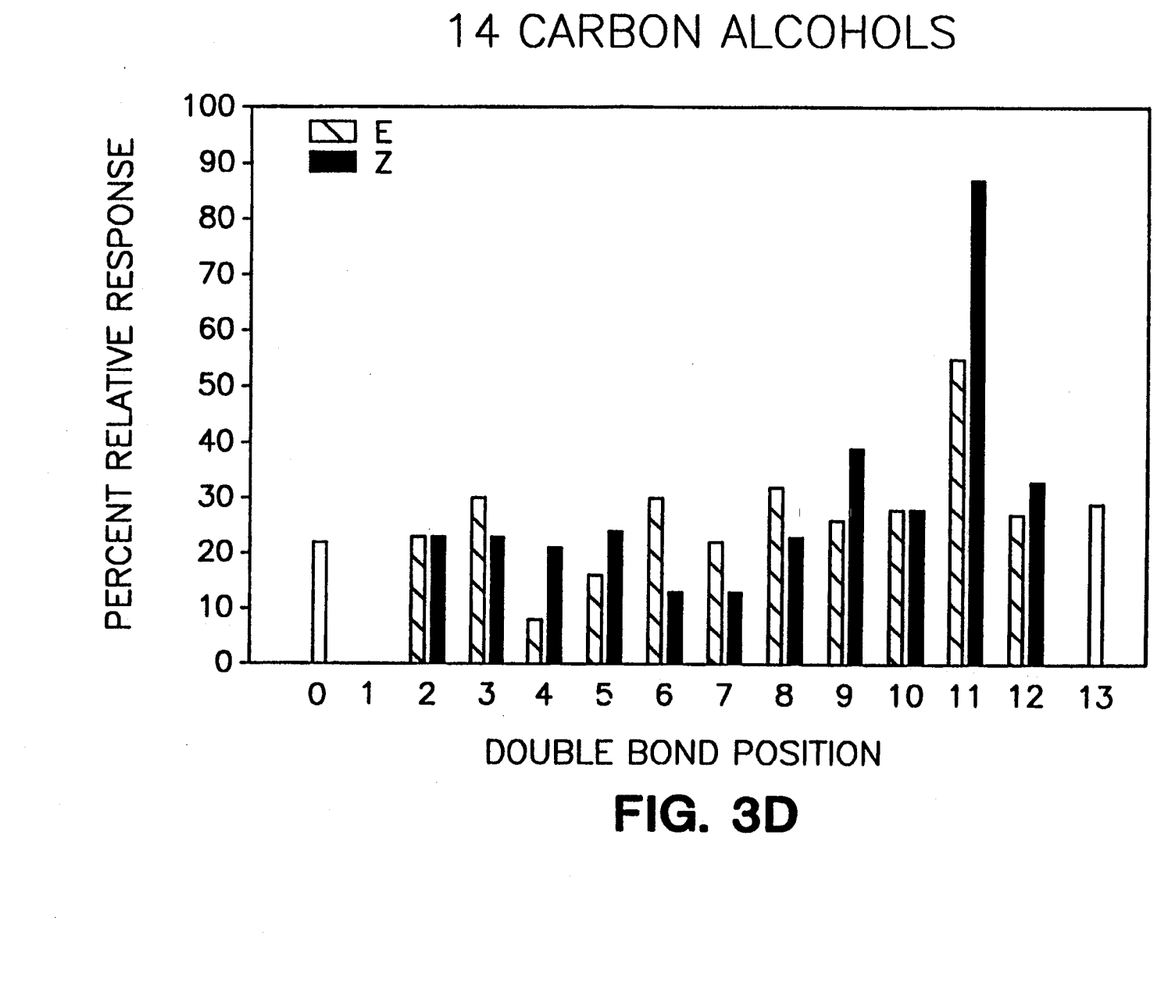

The compounds in the composition are available commercially or can be prepared synthetically in accordance with the procedure described by S. Voerman in *Agric. Ecosystems Environ.* 21 31–41 (1988). The synthesis of I is shown in FIG. 1. In brief, 1,10-decanediol (III) is reacted with concentrated hydrochloric acid. Continuous extraction of the reaction mixture with petroleum ether (b.p. 100°–140° C.) gives 10-chlorodecan-1-ol (IV) free of dichloride. IV is reacted with an equimolar quantity of dihydropyran, catalysed by 1 drop of concentrated hydrochloric acid to produce 1-chloro-10-[(tetrahydro-2H-pyran-2-yl)oxy]decane (V). Butyne gas is bubbled into a solution of n-butyl lithium under nitrogen and then V is added dropwise to produce 14-[(tetrahydro-2H-pyran-2-yl)oxy]-3-tetradecyne (VI). VI is hydrogenated with a P2-nickel catalyst (H. C. Brown and V. K. Ahiya, *J. Chem. Soc. Chem. Comm.*, pp. 553–554 (1973)) to produce the Z olefin, 14-[(tetrahydro-2H-pyran-2-yl)oxy]-(Z)-3-tetradecene (VII), with less than 1% of the E isomer. The pheromone component, I, is generated by heating VII for 15 minutes in methanol containing a few drops of hydrochloric acid. II is prepared according to the scheme shown in FIG. 2. The conversions of 1,8-octanediol (VIII) to (Z)-9-dodecen-1-ol (XIII) is carried out the same as III to I except that VIII is substituted for III. XIII is converted to the pheromone component, II, by reaction with acetic anhydride in pyridine.

The compounds in the two-component attractant composition described above are used in pure or substantially pure form. As used in the specification and the claims, the phrase "pure or substantially pure" means that compounds I and II are substantially free of undesirable masking or inhibitory effects with regard to the intended activity. Other compounds may be added to the composition provided they do not substantially interfere with the intended activity of the two-component composition of the invention. For example, as shown in Example 3, below, the inclusion of (E)-11-tetradecen-1-ol with the two-component attractant composition of the invention did not increase or decrease trap catch over that obtained without the inclusion of this compound. Whether or not a compound interferes with attractant activity can be determined by routine tests in the field as described in Example 3, below. If trap catch is decreased by 2-fold or more when the compound is added to the two-component composition compared to the two-component composition without the added compound, the additive is considered to substantially interfere with attractant activity of the composition.

USE OF THE ATTRACTANT COMPOSITION

The attractant composition of the invention may be used as a detecting agent, monitoring agent, or control agent for the apple ermine moth. In practice, the attractant composition is used as a trap bait or is otherwise applied to a locus of the moths, that is, an area where the moths are present or where they may occur. The trap or lure is placed on an apple tree or within close proximity to an apple tree, that is, within 20 feet of an apple tree. The composition of the invention is used in an amount effective to induce the desired male response. In the case of an attractant response, for example, an effective amount is defined as that quantity of the composition that attracts apple ermine moth males to the location of a bait at a rate significantly higher than males are attracted to a nonbaited location. Under typical field conditions, amounts of 1 to 10,000 $\mu$g per rubber septum (which corresponds to an evaporation rate of 0.006 to 60 $\mu$g per septum per day) and preferably 10 to 1,000 $\mu$g per septum (which corresponds to an evaporation rate of 0.06 to 6 $\mu$g per septum per day) are effective. Factors such as population density, temperature, wind velocity, and rain will influence the response of the moths and thus the actual number of moths trapped. The amount of composition in a particular set of circumstances that will be within an effective range can readily be determined by a dose response field test as described in Example 3, below.

In the case where the desired response is disruption of mating by confusing or inhibiting the male moth, an effective amount is defined as that quantity of the composition which permeates the atmosphere such that males are prevented from orienting to and inseminating the females, i.e., disruption of mating, at a rate significantly higher than disruption of mating of males at a nontreated location. As with the attractant response, factors such as population density, temperature, wind velocity, and rain will influence the actual number of moths disrupted. The exact dose to use in any particular set of circumstances can readily be determined by a dose response field test.

It is envisioned that the attractant composition would be useful in detecting, monitoring, or controlling apple ermine moth populations when used in conjunction with a trap or pheromone disseminator (controlled release substrate) known in the art. Exemplary of such traps are the "Pherocon" 1C wing trap, delta trap, unitrap, or Heliothis trap. The evaporation rate of the attractant composition is controlled by using a controlled release substrate (CRS). We have found that rubber septa are excellent CRS for detection and monitoring. Rubber septa baited with the attractant composition of the invention provide a lure that attacts more males than female baited traps and that lasts for the entire flight season. Typically, the composition is applied to rubber septa in solution in a suitable carrier, that is, one that does not interfere with the activity of the composition, for example, an organic solvent such as hexane or dichloromethane. Examples of other CRS are laminates, polyvinyl chloride pellets, and microcapillaries. A composition of I and II is applied to the CRS to provide a ratio of components in the evaporating vapor of about 99:1 to 91:9 (I:II) and preferably about 98:2 to 95:5 (I:II). Optimum attractant amounts can be readily determined by routine experimentation as illustrated in Example 3, below. CRS used for controlling populations by mating disruption include the aforenamed CRS or other CRS specifically designed for this purpose, e.g., Shin Etsu Corp. "Ropes," containing an effective disruptant amount.

When used as a detection or monitoring agent, traps are baited with the novel composition of the invention and the catch tabulated to determine size and location of infestation. Economic use of appropriate pest management systems can then be determined.

Use of the composition as a control agent can be carried out in several ways. One method is to use the compound to attract the insects to suitable substrates and subsequently or simultaneously expose the moths to insecticides which control the moths. An effective amount of the insecticide is used, that is, an amount that is lethal for an exposed insect or at least sublethal but sufficient to incapacitate the insect in regard to mating activity. Examples of useful insecticides are are carbaryl (1-naphthyl N-methylcarbamate) (sold under the tradename "Sevin" by Rhone-Poulenc Ag. Co. Inc., Research Triangle Park, North Carolina), malathion (sold under the tradename "Cythion" by American Cyanamide Corp.), and azinphos-methyl (sold under the tradename "Guthion"). Insecticides can be used in traps baited with the composition. This eliminates the need to spread the insecticides unnecessarily. It is also envisioned that chemosterilants could be used in conjunction with the composition compound to attract and sterilize male moths.

Another method to control the apple ermine moth using the composition of the invention is to detect the location and boundaries of localized apple ermine moth infestations and employ in the area biological control agents such as parasites or predators of the apple ermine moth. Biological control agents include *Ageniaspis fuscicollis*, *Herpestomus brunnicornis*, *Diagegma armillata*, and *Eurysthaea scutellaris*.

The attractant composition may also be used to control the apple ermine moth by confusion of male moths, thus preventing mating. For example, one technique is to permeate the atmosphere with sufficient compound to prevent males from orienting to and inseminating the females.

Another use of the composition is as a reference composition to distinguish apple ermine moths from other species of small ermine moths.

DISCOVERY OF THE ATTRACTANT COMPOSITION

Discovery of an attractant for the male apple ermine moth presented problems of particular difficulty. As discussed above, the components of the sex pheromone gland extract of the female apple ermine moth had not been identified. Further, investigators that studied the pheromones of other species of small ermine moth (Lofstedt et al., supra,) reported that the pheromone for each of the species was multi-component, and the number, proportion, and type of compounds present was different for each species. Thus, only limited information was available as precedent for elucidation of an attractant for the apple ermine moth. While some EAG and single cell studies of the apple ermine moth had been reported, the predictive value of electrophysiological screening in pheromone identification is limited in multicomponent pheromones (Lofstedt and van der Pers, *Journal of Chemical Ecology*, 11: 649–666, 663 (1985)). Further, as pointed out by van der Pers and den Otter, *Journal of Insect Physiology*, 24: 337–343 (1978) at page 342, sex pheromone receptor cells are not exclusively sensitive to the pheromone but also respond to chemically related substances, such as its geometrical and positional isomer and sexual attractants of related species. Further, a major drawback of EAG studies is that it does not discriminate between attractants and inhibitors or repellents (Hendrikse et al., supra).

In our work to discover an attractant for the male apple ermine moth, we carried out several lines of investigations concurrently: (1) EAG studies of 112 model compounds, (2) gas chromatography-mass spectrometry (GC-MS) and GC-EAG analysis of extracts of female sex pheromone glands, (3) field studies of test compounds and mixtures. Information from one line of investigation was used to modify the research protocol for another line of investigation. In this way we were able to discover an attractant composition and to develop a long lasting, potent lure useful for an entire season. This was done in spite of the extremely small quantities of sex attractant components produced by female apple ermine moths, $5.8 \times 10^{-10}$ g of (Z)-11-tetradecen-1-ol and $3.5 \times 10^{-12}$ g of (Z)-9-dodecen-1-ol acetate per female.

IDENTIFICATION OF COMPONENTS OF THE FEMALE SEX PHEROMONE GLAND EXTRACT

Identification of compounds present in an extract of the female apple ermine moth sex pheromone gland was carried out using gas chromatography (GC) analysis and GC-MS analysis. The procedure is described in detail in Example 1, below. Identification presented problems of particular difficulty. One of the compounds was only present in trace amounts (0.1% of the identified components) and was not initially detected by GC-MS of a female sex pheromone gland extract. It was only detected when the mass spectrometer was placed in the single ion mode (SIM) operational format which allowed the detection of extremely small quantities of compounds searched for.

GC-EAG. Gas chromatographic fractions of extract of sex pheromone glands of 59 female *Y. malinellus* covering the volatility range from the retention time of decanol through octadecyl acetate were collected from a methyl silicone column, and the EAG response to each fraction was determined. Fraction 4 containing the 14-carbon alcohols produced the strongest response (0.8 mv above the blank). A capillary GC trace (methyl silicone column) of extract indicated the presence of tetradecanol, (E)-11-tetradecen-1-ol, and (Z)-11-tetradecen-1-ol in this fraction. The other fractions produced responses ranging from 0.2 to 0.4 mv. Fraction 2, which would contain II and/or (Z)-11-tetradecenal if present, produced the 0.2 mv response. Thus there was not enough II present in the extract to indicate its presence.

GC-MS. In the initial experiment using an extract from 10 female moths, five compounds were found (ratio given in parentheses): tetradecanol (2.0), (E)-11-tetradecen-1-ol (0.37), I (1.0), hexadecanol (1.4), and hexadecyl acetate (0.35). The amount of I in the extract was 5.8 ng. The compound II was not detected.

Next, an extract of the sex pheromone gland of 150 female moths was analyzed by GC-MS in the single ion monitor mode (SIM). The ions monitored were chosen so as to be able to detect II, I, (E)-11-tetradecen-1-ol, and (E,E)-10,12-tetradecen-1-ol. The analysis indicated 14.9 ng of I, 6.5 ng of (E)-11-tetradecen-1-ol, 0.09 ng II (0.6% of I; retention time 12.794 min.; ratio of 61/166 ions=43:57; retention time of II standard was 12.795 min.; ratio of 61/166 ions=45:55; limit of detection 0.05 ng), and no (E,E)-10,12-tetradecen-1-ol.

SURVEY OF MODEL

A survey of 112 test compounds was carried out. The compounds included:

A. Twenty 12-carbon acetate compounds: dodecyl acetate and the 12-carbon alkenyl acetates containing double bonds in all the possible positions (carbon 2–11), and two configurations ((Z) and (E)) for each double bond position, and one configuration for the double bond on carbon 11.

B. Twenty 12-carbon alcohol compounds: dodecanol and the 12-carbon alkenyl alcohols containing double bonds in all the possible positions (carbon 2–11), and two configurations ((Z) and (E)) for each double bond position, and one configuration for the double bond on carbon 11.

C. Twenty-four 14-carbon acetate con,pounds: tetradecyl acetate and the 14-carbon alkenyl acetates containing double bonds in all the possible positions (carbon 2–13), and two configurations ((Z) and (E)) for each double bond position, and one configuration for the double bond on carbon 13.

D. Twenty-four 14-carbon alcohol compounds: tetradecanol and the 14-carbon alkenyl alcohols containing double bonds in all the possible positions (carbon 2–13), and two configurations ((Z) and (E)) for each double bond position, and one configuration for the double bond on carbon 13.

E. Other compounds: (Z)- and (E)-7-, 9-, and 11-tetradecenals and hexadecenals and the (Z)- and (E)-7-, 9-, and 11-hexadecenyl alcohols and acetates.

The EAG response profiles of male apple ermine moths to the n-alkyl and n-alkenyl 12- and 14-carbon alcohols and acetates are given in FIGS. 3A–D. The strongest response was obtained from II and was denoted as 100% relative response. The EAG values of the other model compounds are expressed as a percent of the response to II. Strong responses were obtained from (Z)-11-tetradecen-1-ol acetate (76%) and I (87%). At a dosage of 0.3 ng, (Z)-11-tetradecenal produced a stronger response than I, while at a dosage of 30 ng, I and (Z)-11-tetradecenal produced equal responses.

FIELD TESTS

The field tests are described in detail in Example 3, below. The tests showed that the presence of both I and II are required in the composition for trap catch. Traps baited with the synthetic lure produced better trap catch than traps baited with females.

In sum, the attractant mixture of the invention requires the presence of I and II in the mixture. Compound II has never been reported as a pheromone component for any other species of the small ermine moth. While compound I was reported as present in the multi-component female sex gland extract of six species of small ermine moth, it was only a minor component (Lofstedt et al., supra). Further, in four of the six species where it was found, there was no proven behavioral activity (Lofstedt et al., supra).

Another surprising discovery is that although the natural pheromone of male apple ermine moths was found to contain a mixture of six compounds, II was only present in a trace amount, about 0.1% of the six pheromone gland components. Further, when tetradecan-1-ol, the most abundant compound found in the pheromone gland, or (E)-11-tetradecen-1-ol, also present in the pheromone gland in a greater amount than II, was added to the two-component sex attractant of the invention, neither increased trap catch. Additionally, the test compounds, (Z)-11-tetradecenal or (Z)-11-tetradecen-1-ol acetate, which were found to elicit a strong EAG response of male apple ermine moths, did not increase trap catch when added to the two-component sex attractant.

Another surprising discovery is that while neither compound alone produced trap catch in the field, the composition demonstrated biological activity toward apple ermine moth males comparable to or greater than female moths.

EXAMPLES

The following examples are intended only to further illustrate the invention and are not intended to limit the scope of the invention which is defined by the claims.

EXAMPLE 1

Identification of Pheromone

Insect Collection and Handling. Larvae and pupae of apple ermine moths in their tents were collected from infested apple trees in an orchard near Bellingham, Wash., USA, placed in sealed containers, and transported to a quarantine rearing facility in Yakima. The tents were divided into parts, each containing several cocoons, and each part was placed on moist peat moss in a closed container. The room was maintained at 50% RH and 20° C. with a 16:8 light-dark cycle. Adults were collected daily 3 hours after onset of photophase and sexed. The females were maintained in separate glass vials while the males were maintained together in cages, and both sexes were provided with a 10% sugar solution.

Collection of Pheromone. Calling female moths (6–7 days old) were collected 3–4 hours into photophase and chilled in a refrigerator for about 10 minutes to inactivate them. Terminal abdominal segments were severed and steeped for 15 minutes in dichloromethane, and the solution was removed with a syringe and stored at −20° C. until used.

Identification of Natural Pheromone.

Isolation of Fractions by Gas Chromatography. Fractions of female sex pheromone gland (SPG) extract for EAG analysis were collected from a GC equipped with a megabore capillary column (methyl silicone; DB-1; 15 m×0.53 mm I.D.; J & W Scientific, Folsom, Calif.) connected to a glass-lined splitter sending 1 part of effluent to the detector and 9 parts to the collector. The GC was programmed at 2°/min from 120° to 210° C. Ten fractions encompassing the retention time of decanol through octadecyl acetate were collected as follows, (fraction) time interval in minutes: (1) 5–15.5; (2) 15.5–18; (3) 18–21; (4) 21–24; (5) 24–27.5; (6) 27.5–32; (7) 32–37.5; (8) 37.5–43; (9) 43–47; (10) 47–53. The retention time in minutes of synthetic reference compounds were: decanol, 5.5; dedecanol, 7.9; dedecyl acetate, 17.3; I, 21.8; tetradecyl acetate, 31.0; hexadecyl acetate, 42.2; octadecanol, 47.1; octadecyl acetate, 51.7. GC analysis of SPG extract was accomplished with a capillary column (methyl silicone; DB-1; 60 m×0.25 mm; J & W Scientific, Folsom, Calif.) operated at 180° C.

Electroantennographic (EAG) Response to GC Fractions. Gas chromatographic fractions of extract of sex pheromone glands of 59 female apple ermine moths covering the volatility range from the retention time of decanol through octadecyl acetate were collected from a methyl silicone column, and the EAG response to each fraction was determined. Fraction 4 containing the 14-carbon alcohols produced the strongest response (0.8 mv above the blank). A capillary GC trace (methyl silicons column) of extract indicated the presence of tetradecan-1-ol, (E)-11-tetradecen-1-ol, and I in this fraction. The other fractions produced responses ranging from 0.2 to 0.4 mv.

Liquid Chromatography of Pheromone Extract. An extract of 150 female SPG was chromatographed on a column of silica gel (0.6 g). The column was eluted successively with hexane, hexane-dichloromethane (70:30), and dichloromethane. The hexane-dichloromethane (70:30) and dichloromethane fractions containing esters and alcohols were combined and concentrated for GC-MS analysis.

Identification by Mass Spectrometry. A Hewlett-Packard (Avondale, Pa.) gas chromatograph (model 5790) with a quadrapole mass selective detector (model 5970) was equipped with a capillary column (DB-Wax; 60 m×0.25 mm I.D.; J & W Scientific, Folsom, Calif.). When the gland extract of 10 female apple ermine moths was analyzed, the column was held at 80° for 2 minutes and programmed at 20°/minute to 200° and maintained at that temperature. Total ion abundance from m/z=15 to m/z=300 was monitored. When the cleaned-up extract of 150 females was analyzed in the single ion monitor mode (SIM), the same temperature program was used, but ions 61 and 166 were monitored between 12 and 17 minutes (II standard at 12.78 minutes), ions 68, 166, and 194 were monitored between 17 and 20 minutes (I standard at 18.10 minutes), and ions 81 and 210 were monitored between 20 and 28 minutes ((E,E)-10,12-tetradecadien-1-ol standard at 24.03 minutes).

A GC-MS analysis of the extract of SPGs from 10 females showed the presence of the following compounds in the given ratios: tetradecan-1-ol (2.0), (E)-11-tetradecen-1-ol (0.37), I (1.0), hexadecan-1-ol (1.4), and hexadecan-1-ol acetate (0.35). The amount of I in the extract was 5.8 ng. An extract of SPGs from 150 females was partially purified by liquid chromatography. The alcohol and ester fractions were combined, concentrated, and analyzed by GC-MS(SIM). The ions monitored were chosen so as to be able to detect II, I, (E)-11-tetradecen-1-ol, and (E,E)-10,12-tetradecadien-1-ol. The analysis indicated 14.9 ng of I, 6.5 ng of (E)-11-tetradecen-1-ol, 0.09 ng of II (0.6% of I; retention time 12.794 minutes; ratio of 61/166 ions=43:57; retention time of II standard was 12.795 minutes; ratio of 61/166 ions=45:55; limit of detection 0.05 ng), and no (E,E)-10,12-tetradecadien-1-ol.

EXAMPLE 2

EAG Studies of Model Compounds

A survey of 112 test compounds was carried out. The compounds included:

A. Twenty 12-carbon acetate compounds: dodecyl acetate and the 12-carbon alkenyl acetates containing double bonds in all the possible positions (carbon 2–11), and two configurations ((Z) and (E)) for each double bond position, and one configuration for the double bond on carbon 11.

B. Twenty 12-carbon alcohol compounds: dedecanol and the 12-carbon alkenyl alcohols containing double bonds in all the possible positions (carbon 2–11), and two configurations ((Z) and (E)) for each double bond position, and one configuration for the double bond on carbon 11.

C. Twenty-four 14-carbon acetate compounds: tetradecyl acetate and the 14-carbon alkenyl acetates containing double bonds in all the possible positions (carbon 2–13), and two configurations ((Z) and (E)) for each double bond position, and one configuration for the double bond on carbon 13.

D. Twenty-four 14-carbon alcohol compounds: tetradecanol and the 14-carbon alkenyl alcohols containing double bonds in all the possible positions (carbon 2–13), and two configurations ((Z) and (E)) for each double bond position, and one configuration for the double bond on carbon 13.

E. Other compounds: (Z)- and (E)-7-, 9-, and 11-tetradecenals and hexadecenals and the (Z)- and (E)-7-, 9-, and 11-hexadecenyl alcohols and acetates.

The experimental apparatus was as described by McDonough et al., *Journal of Chemical Ecology* 6: 565–572 (1980). Test cartridges for the EAG profiles were loaded with 60 μg of model compound. Duplicate determinations were made for each datum point both in the EAG profile and in the concentration study. The model compounds were obtained commercially or were prepared and purified by established synthetic methodology (Voerman, supra). They were at least 98% pure by gas chromatographic analysis, and contained 1% or less of the geometrical isomer.

The EAG response profiles of male apple ermine moths to the n-alkyl and n-alkenyl 12- and 14-carbon alcohols and acetates are given in FIG. 3. The strongest response was obtained from II and was denoted as 100% relative response. The EAG values of the other model compounds are expressed as a percent of the response to II. Strong responses were obtained from I (87%) and (Z)-11-tetradecen-1-ol acetate (76%). Of the other compounds tested, only (Z)-11-tetradecenal produced a strong response (85% of II).

To better evaluate the relative potency of the compounds producing strong EAG responses, EAG measurements were made at dosages of 0.1, 0.3, 1.0, 3.0, 10.0, and 30.0 ng/test cartridge. (Z)-11-tetradecenal, I, and II gave excellent linear correlations for EAG response versus logarithm of the dosage. The EAG responses in mv at a dosage of 1 ng showed the order to be II>(Z)-11-tetradecenal>I>(Z)-11-tetradecen-1-ol acetate (Table 1). Because of the differing slopes of the regression line (EAG response=m logarithm dose+constant), I and (Z)-11-tetradecenal produced approximately equivalent responses at dosages above 30 ng.

TABLE 1

| Compound | EAG response in mv at 1 ng dose |
| --- | --- |
| (Z)-11-tetradecen-1-ol (I) | 0.442 |
| (Z)-11-tetradecenal | 0.620 |
| (Z)-9-dodecen-1-ol acetate (II) | 0.960 |
| (Z)-11-tetradecen-1-ol acetate | 0.287 |

EXAMPLE 3

Field Tests

Field tests were conducted in a block of 18 apple trees near Bellingham, Wash. Test chemicals in 100 μl dichloromethane were dissolved in rubber septa (West Co., Phoenixville, Pa.), and placed in "Pherocon" 1C traps (Trece, Corp., Salinas, Calif.). The traps were hung in the upper one-third of the canopy of each tree. Three replicates of 6 test lures were randomly drawn for trap positions. Each week the number of males in the traps was counted and the traps were replaced. In the test with female apple ermine moths as the bait, three females in a screened cage were placed in each trap.

Table 2 shows the captures of adult male apple ermine moths in traps baited with various candidate lures. There were three replicates per test lure. In each test numbers followed by the same letter were not significantly different (p=0.05) by Duncan's Multiple Range Test.

In Test 1 (Table 2) traps baited with I+(E)-11-tetradecen-1-ol, did not catch significant numbers of males, whereas traps baited with the 3-component lure, I, +(E)-11-tetradecen-1-ol+II caught large numbers of males. When the dosage was 100:30:1, catches exceeded those of traps baited with females. All of the females were alive at the end of the test. Traps baited with the 3-component lure caught as many males as the traps baited with the three components plus (Z)11-tetradecenal (Test 2). Test 3 showed that both I and II must be present to produce trap catch, but the presence or absence of (E)-11-tetradecen-1-ol had no effect on trap catch. Various combinations of I+(E)-11-tetradecen-1-ol+(Z)-11-tetradecen-1-ol acetate did not produce trap catch even though I+(E)-11-tetradecen-1-ol+II produced a very high capture (Test 4). Dosages of I+II (100:1), ranging over a factor of 100, produced equivalent catch (Test 5). Also, ratios of I to II of 100:0.5 to 100:1.5 and perhaps to 100:2.5 produced equivalent trap catch (Test 6), and ratios of 100:0.3 and 100:3 produced lower catch (Test 1).

TABLE 2

| Test No. | Lure | Dosage (μg/septum) | Cumulative Captures |
| --- | --- | --- | --- |
| 1 | 13–19 July 1988 | | |
| | I + (E)-11-tetradecen-1-ol | 100:30 | 1c |
| | I + (E)-11-tetradecen-1-ol + II | 100:30:0.3 | 53b |
| | I + (E)-11-tetradecen-1-ol + II | 100:30:1.0 | 163a |
| | I + (E)-11-tetradecen-1-ol + II | 100:30:3.0 | 84b |
| | Females | | 88b |
| | Blanks | | 0c |
| 2 | 20–26 July 1988 | | |
| | I + (E)-11-tetradecen-1-ol + II | 100:30:1 | 92a |
| | I + (E)-11-tetradecen-1-ol + II + (Z)-11-tetradecenal | 100:30:1:0.1 | 56a |
| | I + (E)-11-tetradecen-1-ol + II + (Z)-11-tetradecenal | 100:30:1:0.3 | 94a |
| | I + (E)-11-tetradecen-1-ol + II + (Z)-11-tetradecenal | 100:30:1:1.0 | 90a |
| | I + (E)-11-tetradecen-1-ol + II + (Z)-11-tetradecenal | 100:30:1:3.0 | 117a |
| | Blanks | | 0b |
| 3 | 27 July–1 Aug 1988 | | |
| | I + (E)-11-tetradecen-1-ol + II | 100:30:1 | 70a |
| | I + II | 100:1 | 79a |
| | (E)-11-tetradecen-1-ol + II | 30:1 | 0b |
| | II | 1 | 0b |
| | II | 10 | 0b |
| | Blanks | | 0b |
| 4 | 1–7 August 1988 | | |
| | I + (E)-11-tetradecen-1-ol + II | 100:30:1 | 264a |
| | I + (E)-11-tetradecen-1-ol + (Z)-11-tetradecen-1-ol acetate | 100:30:0.75 | 1b |
| | I + (E)-11-tetradecen-1-ol + (Z)-11-tetradecen-1-ol acetate | 100:30:2.25 | 0b |
| | I + (E)-11-tetradecen-1-ol + (Z)-11-tetradecen-1-ol acetate | 100:30:7.5 | 0b |
| | I + (E)-11-tetradecen-1-ol + (Z)-11-tetradecen-1-ol acetate | 100:30:22.5 | 0b |
| | Blanks | | 0b |
| 5 | 8–14 August 1988 | | |
| | I + II | 10:0.1 | 74a |
| | I + II | 30:0.3 | 78a |
| | I + II | 100:1 | 81a |
| | I + II | 300:3 | 108a |
| | I + II | 1,000:10 | 92a |
| | Blanks | | 0b |
| 6 | 15–22 August 1988 | | |
| | I + II | 300:1.5 | 17a |
| | I + II | 300:3.0 | 19a |
| | I + II | 300:4.5 | 21a |
| | I + II | 300:6.0 | 12ab |
| | I + II | 300:7.5 | 7ab |
| | Blanks | | 1b |

It is understood that the foregoing detailed description is given merely by way of illustration and that modification and variations may be made within without departing from the spirit and scope of the invention.

Having thus described the invention, we claim:

1. A method of attracting male apple ermine moths, which comprises placing in a locus of male apple ermine moths a controlled release substrate (CRS) having an effective attractant amount of a composition comprising pure or substantially pure (Z)-11-tetradecen-1-ol (I) and pure or substantially pure (Z)-9-dodecen-1-ol acetate (II) mixed in a ratio to provide a vapor evaporating from said CRS having a ratio of I:II of about 99:1 to 91:9.

2. The method of claim 1 where said vapor has a ratio of I:II of 98:2 to 95:5.

3. The method of claim 1 wherein said CRS is a rubber septum and said composition comprises a ratio of I:II of 100:0.3 to 100:2.5.

4. The method of claim 1 wherein said CRS is a rubber septum and said composition comprises a ratio of I:II of 100:0.5 to 100:1.5.

5. A method of disruption of mating of apple ermine moths, which comprises applying to the locus of male apple ermine moths an effective disruptant amount of a composition which comprises a mixture of pure or substantially pure (Z)-11-tetradecen-1-ol (I) and pure or substantially pure (Z)-9-dodecen-1-ol acetate (II) in a weight ratio range of about 100:0.3 to 100:2.5 (I:II).

6. A method for trapping male apple ermine moths, which comprises baiting a trap with an effective attractant amount of a composition which comprises a mixture of pure or substantially pure (Z)-11-tetradecen-1-ol (I) and pure or substantially pure (Z)-9-dodecen-1-ol acetate (II) in a weight ratio range of about 100:0.3 to 100:2.5 (I:II).

* * * * *